(12) United States Patent
Vancamberg et al.

(10) Patent No.: US 10,993,706 B2
(45) Date of Patent: May 4, 2021

(54) BIOPSY METHOD AND ASSOCIATED BIOPSY DEVICE

(71) Applicant: GENERAL ELECTRIC COMPANY, Schenectady, NY (US)

(72) Inventors: Laurence Vancamberg, Buc (FR); Serge Muller, Buc (FR); Guillaume Peter, Buc (FR); Marcia C. Hill, Vero Beach, FL (US); Aurélie Boudier, Buc (FR); Romain Moulin, Buc (FR); Aurora Talaverano Fuentes, Madrid (ES)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 175 days.

(21) Appl. No.: 15/313,845

(22) PCT Filed: May 28, 2014

(86) PCT No.: PCT/IB2014/001528
§ 371 (c)(1),
(2) Date: Nov. 23, 2016

(87) PCT Pub. No.: WO2015/181577
PCT Pub. Date: Dec. 3, 2015

(65) Prior Publication Data
US 2017/0202544 A1    Jul. 20, 2017

(51) Int. Cl.
*A61B 10/02* (2006.01)
*A61B 90/17* (2016.01)
*A61B 90/11* (2016.01)
*A61B 17/34* (2006.01)

(52) U.S. Cl.
CPC .......... *A61B 10/0233* (2013.01); *A61B 90/11* (2016.02); *A61B 90/17* (2016.02); *A61B 2017/3409* (2013.01)

(58) Field of Classification Search
CPC ..... A61B 90/17; A61B 10/0233; A61B 6/502; A61B 90/11; A61B 2017/3409
See application file for complete search history.

(56) References Cited

U.S. PATENT DOCUMENTS

| 4,798,212 A | 1/1989 | Arana |
| 5,386,447 A | 1/1995 | Siczek |
| 6,102,866 A | 8/2000 | Nields et al. |
| 2007/0250047 A1 | 10/2007 | Harter |

(Continued)

FOREIGN PATENT DOCUMENTS

| CN | 101044992 A | 10/2007 |
| CN | 101066214 A | 11/2007 |
| CN | 102481146 A | 5/2012 |

OTHER PUBLICATIONS

International Search Report and Written Opinion for PCT/IB2014/001528, dated Jan. 28, 2015, 9 pages.

(Continued)

*Primary Examiner* — Patrick Fernandes
(74) *Attorney, Agent, or Firm* — Fletcher Yoder, P.C.

(57) ABSTRACT

This invention relates to a biopsy method comprising automated moving of at least part of a biopsy sampler within a biopsy volume, to perform a biopsy in a zone of interest in a body, wherein said automated moving is preceded by variable positioning of said biopsy volume.

11 Claims, 6 Drawing Sheets

(56) References Cited

U.S. PATENT DOCUMENTS

| | | |
|---|---|---|
| 2008/0103387 A1 | 5/2008 | Gross |
| 2009/0143672 A1 | 6/2009 | Harms et al. |
| 2011/0087132 A1 | 4/2011 | DeFreitas et al. |
| 2012/0095329 A1 | 4/2012 | Kamiya |
| 2013/0101083 A1* | 4/2013 | O'Connor .............. G21K 1/025 378/37 |

OTHER PUBLICATIONS

First Office Action and Search issued in connection with corresponding CN Application No. 201480079327.0 dated Dec. 5, 2018 (English Translation Unavailable).

* cited by examiner

BIOPSY METHOD AND ASSOCIATED BIOPSY DEVICE

CROSS-REFERENCE TO RELATED APPLICATIONS

This application is a US PCT National Phase filing under 35 U.S.C. 371 of co-pending International Application No. PCT/IB2014/001528, filed May 28, 2014, which is incorporated herein by reference in its entirety.

FIELD OF THE INVENTION

The invention relates to biopsy methods and associated biopsy devices, used to perform a biopsy in a human body, preferably in the breast of a human body.

BACKGROUND OF THE INVENTION

The biopsy method technical problem and associated solution will be described in relation to breast biopsy in order to be more concrete and clearer. However, these biopsy method technical problem and solution may be used for other organs of a human body. They will be all the more interesting than the considered organ can be of a broadly varying size and all the more interesting than the considered organ can lead to many different patient positions depending on the part of the organ to be accessed by the biopsy device.

According to a first prior art, it is known to provide for paddles with different biopsy volumes for a two dimensional (2D) localization associated to biopsy sampler moved manually and directly by the practitioner within the biopsy volume. This completely manual biopsy method moving manually the biopsy sampler does provide neither for sufficient precision nor for repeatability. Here, the biopsy volume is simply an indication of a zone where the lesion should be, and not really a biopsy volume within which the moving of the biopsy sampler would be automatically delimited, let alone automated.

According to a second prior art, it is known to use a fixed paddle with a unique fixed biopsy volume for three dimensional (3D) localization associated to automated biopsy sampler moving within said biopsy volume. However, the unique fixed position of the biopsy volume relative to the breast support implies several constraints, at least part of them being relatively hard to get rid of.

A first problem of this second prior art deals with the fact that the fixed position of the biopsy volume leads to many breast manipulations by radiologist in order to check that the lesion is on the one side within the biopsy volume and on the other side at a place where the biopsy sampler can easily reach the lesion and perform the biopsy in the lesion. The current biopsy volume is centered in X direction which is the direction parallel to the length of the chest wall of the detector. Therefore, the radiologist has to manipulate the breast in order to position the lesion correctly in the biopsy volume. This task is not easy and may become particularly difficult depending on the type of breast and on the place of the lesion within the breast. So, in a nutshell, first in order to position the patient and second to position the lesion inside this biopsy volume, the radiologist has to manipulate a lot the breast of the patient. It is indeed the patient who must adapt herself to the apparatus.

A second problem of this second prior art deals with the extreme size of some breast which leads first to uncomfortable position of breast patient and/or second to a breast position which is not well maintained in the case of a breast lesion located near the nipple. To be more precise, for small breasts with a lesion near the nipple, there is not enough breast tissue to compress it correctly between paddle and breast support, so it hurts the patient and the breast slips away. For large breasts, an important part of the breast is hanging out of the breast support. A partial but still uncomfortable solution to adapt for large breasts would require having a biopsy paddle with a larger hole. Anyway, the biopsy volume is still centered in direction X and near the chest wall of the detector, thereby limiting patient positioning. Therefore, for large breasts, the radiologist is putting her hands to support the part of the breast hanging out the breast support.

A third problem of this second prior art deals with an extreme position of the lesion within the breast leading to uncomfortable position of patient, not only for large or small breasts, but also for usual breasts. When the lesion is in the vicinity of the very upper part of the breast or in the vicinity of the very lower part of the breast, positioning of the patient will be uncomfortable too, whatever the size of the breast.

A fourth problem of this second prior art deals with the lateral approach of the needle which may be required for some breast lesions close to the chest wall of the detector and which needs some accessories to be performed correctly and to avoid collisions. For the lateral approach, when the gun risks colliding with the detector, the radiologist puts a box playing the part of a chock under the breast, to cancel such collision risk. However, this is not practical for the radiologist and anyway rather uncomfortable for the patient.

SUMMARY OF THE INVENTION

An object of the present invention is to alleviate at least partly the above mentioned drawbacks.

More particularly, embodiments of the invention aim to provide for a biopsy method and a biopsy device allowing for a biopsy performance which will be more practical for the radiologist and more comfortable for the patient, especially in case of lesions located at extreme positions in the breast and/or in case of lesions located in breasts of extreme size. Therefore, instead of adapting the patient as well as the patient breast to the apparatus performing the biopsy, the solution provided by embodiments of the invention will adapt the apparatus to the specific patient breast and to the specific location of the lesion within this patient breast, by providing for a variable positioning of the biopsy volume, and particularly variable with respect to the breast support location. As already explained, biopsy method and a biopsy device according to embodiments of the invention are not limited to a patient breast, but can be used in relation to other organs of human body, and even in relation to an animal body.

One embodiment of the invention proposes a variable biopsy volume allowing for 3D localization associated to automated biopsy sampler guide moving within said biopsy volume. Thereby, for most of the range of breast sizes, as well as for most of the potential locations of lesion within the breast, it will become both easier to perform a biopsy for the radiologist and more comfortable for the patient to undergo such a biopsy. Computation of a 3D localization of the lesion just before performing the biopsy ensures that the automated biopsy sampler guide moving will be very precise and that the biopsy will be performed in the targeted lesion as scheduled by the radiologist.

In some embodiments of the invention, the proposed biopsy system allows to position the biopsy volume either anywhere on the breast support or at least in several preset positions, by displacing this biopsy volume, at least in a plane parallel to the plane of the breast support. Thereby, the proposed biopsy system can adapt more easily both to the patient morphology and to the lesion position within the patient.

At least one advantage of embodiments of the invention, it is easier for the radiologist to position the patient which in turn can be installed in a more comfortable position. Besides, if the lesion is not in the biopsy volume, this biopsy volume can be moved instead of moving the breast. Any breast, even the thin one, can be biopsied with the lateral approach, without a need of adding a chock under the breast.

Despite its apparent simplicity, i.e. moving the biopsy volume which was fixed earlier in automated biopsy sampler guide moving within this biopsy volume, a solution proposed by embodiments of this invention looks like a leapfrog in the field of biopsy method and of biopsy device, rendering this biopsy performance much easier for the radiologist and much more comfortable for the patient. Indeed, for the man skilled in the art, there was still at least a prejudice to overcome, i.e. providing for two different moves, variable biopsy volume positioning and moving of biopsy sampler guide within the biopsy volume, whereas in the prior art, providing for a single move of the biopsy sampler guide within a fixed biopsy volume (relative to the breast support) appeared to be sufficient to perform the biopsy.

This object is achieved with a biopsy method comprising automated moving of at least part of a biopsy sampler within a biopsy volume, to perform a biopsy in a zone of interest in a body, wherein said automated moving is preceded by variable positioning of said biopsy volume.

This object is also achieved with a biopsy method comprising: determining, above a breast support, a biopsy volume encompassing a zone of interest in a body, using an imaging system, at least part of said body, to localize said zone of interest within said biopsy volume, automated moving of at least part of a biopsy sampler, within said biopsy volume, to perform a biopsy in said localized zone of interest, wherein said determining includes variable positioning, in the plane of said breast support, of said biopsy volume.

This object is still achieved with a biopsy device comprising a biopsy sampler guide adapted to move in an automated way within said biopsy volume, to perform a biopsy in a zone of interest of a body, wherein it also comprises a system adapted to variably position said biopsy volume.

In some embodiments, said at least part of a biopsy sampler is a biopsy sampler guide. Once the moving of the biopsy sampler guide is ended and the biopsy sampler guide is at its final position, the radiologist will introduce the gun including the needle adapted to perform the biopsy in the biopsy sampler guide and secure it.

Embodiments may comprise one or more of the following features, which can be taken separately or together, either in partial combination or in full combination, with any of the preceding objects.

In some embodiments, automated moving is preceded by variable positioning of said biopsy volume in the plane of a breast support. The plane of said breast support is parallel to the sensitive surface of the detector having imaged said zone of interest to localize it. In another option, the detector may tilt with respect to the breast support, in order to keep its sensitive surface perpendicular to main direction of radiation emitted by the source. In the second prior art, some variation of the biopsy volume size in the Z direction above the breast support, that is to say perpendicular to the plane of the breast support, is possible. In the second prior art, indeed, the compression of the breast between breast support and paddle makes a variation in the height of the biopsy volume which position remains fixed, in particular in the plane of the breast support. In this embodiment of the invention, the variation of the position of the biopsy volume, especially in the plane of the breast support, gives the freedom of move which will alleviate the most stringent breast positioning constraints of the second prior art. A variable positioning of said biopsy volume in the plane of a breast support means a variable positioning of said biopsy volume in a plane parallel to the surface of a breast support, so also usually in a plane parallel to the average plane of the breast support which is roughly flat.

There are three degrees of freedom for translational moves. The two most interesting ones are direction X and direction Y which are orthogonal in the plane of the breast support, and direction Z which is perpendicular to the plane of the breast support and which is vertical while the plane of the breast support is horizontal. The compression of the breast is performed by a vertical translation of the paddle towards the surface of the breast support. X direction goes laterally with respect to the breast, whereas Y direction extends from chest to nipple. In other words, X direction is parallel to the chest wall of the breast support, whereas Y direction is perpendicular to the chest wall of the breast support.

In an embodiment, the biopsy volume is included in a volume delimited by a hole in a paddle facing said detector. This paddle is movable along a direction Z perpendicular to the plane XY of the breast support and the average plane of the rather flat paddle remains parallel to the plane of the breast support during this vertical moving. To perform the biopsy, the breast is compressed between the breast support and the paddle.

In a first group of embodiments, said paddle is moving relative to said breast support at least in the plane of said breast support and said paddle comprises preferably only one hole. To make the biopsy volume positioning easily variable, the paddle itself is movable in the plane of the breast support. This first group of embodiments is more practical for the radiologist and/or more comfortable for the patient than the second group of embodiments detailed later.

In a first embodiment, said biopsy sampler guide being linked by a biopsy holder to an imaging system comprising said breast support, a detector and an emitter, said biopsy holder is fixed relative to said breast support. The paddle moving is independent from the biopsy holder which remains immobile in the plane of the breast support. This is the best compromise achieved between practicability of the biopsy system and its complexity.

In a second embodiment, said biopsy sampler guide being linked by a biopsy holder to an imaging system supporting said breast support, said biopsy holder is fixed relative to said paddle. Indeed, the biopsy holder and the paddle are solidary attached with each other. When the breast is compressed between paddle and breast support, a force is exerted upwards by the breast on the paddle which in turn transmits this force to the biopsy holder. Therefore, this biopsy holder should be rigidly mounted on the imaging system so as to avoid that the exerted force displaces the biopsy holder, thereby running the risk of losing precision for the positioning of the biopsy sampler guide held by the biopsy holder.

In a third embodiment, said biopsy sampler guide being linked by a biopsy holder to an imaging system supporting said breast support, said biopsy holder is moving relative to said breast support and is moving independently from said paddle. In order to get mowing of the biopsy volume and of the biopsy sampler guide, there are three different translations or rotations in the plane of the breast support, which are the moving of the biopsy holder, of the biopsy sampler guide and of the paddle.

In a second group of embodiments, said paddle is fixed relative to said breast support in the plane of said breast support. Paddle can however move relative to said breast support perpendicularly to the plane of said breast support. The structure of the biopsy system is simpler than in the first group of embodiments.

In a fourth embodiment, said paddle comprises several holes at different places in the plane of said breast support, said variable positioning being obtained by choosing one of said holes for said automated moving of said biopsy sampler guide. The paddle is a multiple-holes paddle with different biopsy volumes respectively associated to the different holes. This fourth embodiment is more practical for the radiologist, who has no change of paddle to do, than the fifth embodiment.

In a fifth embodiment, said paddle comprises one hole at a given place in the plane of said breast support, there being a set of several paddles having respective given places which are different from one another and being able to be alternatively set up, said variable positioning being obtained by choosing one of said paddles to set it up. This is a set of multiple paddles with different biopsy volumes respectively associated to the different paddles. This fifth embodiment is more comfortable for the patient, because the paddle contains only one hole of limited size, than the fourth embodiment which presents several holes with crossings in between, those crossings being less comfortable for the patient since they press the breast of the patient concentrating the pressure on a limited spot on the breast. If holes are too numerous or too big, the crossings in between will be fine and the pressure they exert on the breast may even become more or less painful for the patient.

In a sixth embodiment, which can be easily combined with the four first embodiments, said paddle comprises one hole at a given place in the plane of said breast support, said variable positioning being obtained by manually or automatically rotating said paddle around an axis perpendicular to the plane of said breast support. The rotation is performed around an axis which is the Z direction perpendicular to the plane of the breast support. In an option, this rotation may be automated too.

In an embodiment the variable positioning includes at least one translation in the plane of said breast support. For example, variable positioning includes a translation along X direction (parallel to the chest wall of the breast support) or a translation along Y direction (perpendicular to the chest wall of the breast support). For example, variable positioning may include only one translation along X direction according to any of the four first embodiments and a rotation around Z direction of half a turn according to sixth embodiment which would have the same effect than a discrete translation along Y direction. In case of only one translation, said translation is discrete or continuous. Discrete translation makes easier the synchronization of the biopsy sampler guide moving to the imaging made just before to localize the lesion. Continuous translation makes more comfortable the positioning of the patient because of the highest capability to adapt to any breast size or to any lesion position within the breast.

In an embodiment, the variable positioning includes two translations in the plane of said breast support which are orthogonal to each other. For example, variable positioning includes a translation along X direction and a translation along Y direction. The translation along X direction allows for a better adaptation to any location of lesion within the breast whereas the translation along Y direction allows for a better adaptation to any size of breast. Y direction extends from chest to nipple whereas X direction extends laterally from one side to the other side of the breast, either upwards and downwards when the patient is lying on her side, or from left to right and vice versa when the patient is standing or sitting.

In case of two translations, both said translations are discrete or both said translations are continuous or one of said translations is discrete while the other of said translations is continuous. The translation along X direction is continuous which may increase comfort of the patient for most locations of lesion within the breast, whereas the translation along Y is discrete, for example with only two positions, presenting one position close to the chest wall of the detector for breasts of average size and one position far from the chest wall of the detector for breasts of either large or small size.

In an embodiment, the zone of interest is imaged by the reception on said detector of a radiation emitted by an emitter moving in a plane perpendicular to the plane of said detector, in order to perform different imaging for more accurate localization of said zone of interest and/or in order to adapt to said variable positioning.

In an embodiment, the said emitter moves along an arc of circle contained in a plane perpendicular to the plane of said detector.

In an embodiment, the biopsy device also comprises a detector adapted to image said zone of interest to localize it within said biopsy volume, and said system is adapted to variably position said biopsy volume in the plane of said breast support.

In an embodiment, the detector is an X-ray detector. Lesion within the breast is imaged so as to be localized. Then the biopsy sampler guide moves within the biopsy volume precisely relative to the localized lesion in the breast.

In an embodiment, the body is a human body. The part of a body is a breast, where at least part of the breast is imaged on said detector.

In an embodiment, the detector is a digital detector, for which imaging of a part of a body can be made on most of its sensitive surface and not only on a very limited spot which was the case with analog detector. Embodiments of the invention are easier to implement with a digital detector which has less constraints, as to imaging for localization on the sensitive surface of the detector, than an analog detector.

In an embodiment, imaging is performed for at least two positions of the source along X direction, or for more than two positions of the source in the ZX plane. Two or more 2D images corresponding to different source positions may be used to rebuild a 3D image of the lesion and of its vicinity within the breast. For example, the biopsy volume is positioned in order to have the image acquired at +/−15° on the same sensitive surface of the detector. The targeted lesion is located in these two 2D images to compute 3D coordinates of the targeted lesion.

In an embodiment, imaging is performed under several different source positions, for example between 5 and 15 positions of source radiation emission, so as to allow for a three dimensional reconstruction by treatment of imaging performed under several angles.

In an embodiment, said variable positioning of said biopsy volume is adapted so as to position said biopsy volume close to at least an edge of a breast support. That way, lateral approach may be performed with no risk of collision between biopsy sampler and breast support. The security is thereby maximized.

Further features and advantages of the invention will appear from the following description of embodiments of the invention, given as non-limiting examples, with reference to the accompanying drawings listed hereunder.

DETAILED DESCRIPTION OF THE INVENTION

Figure 1:
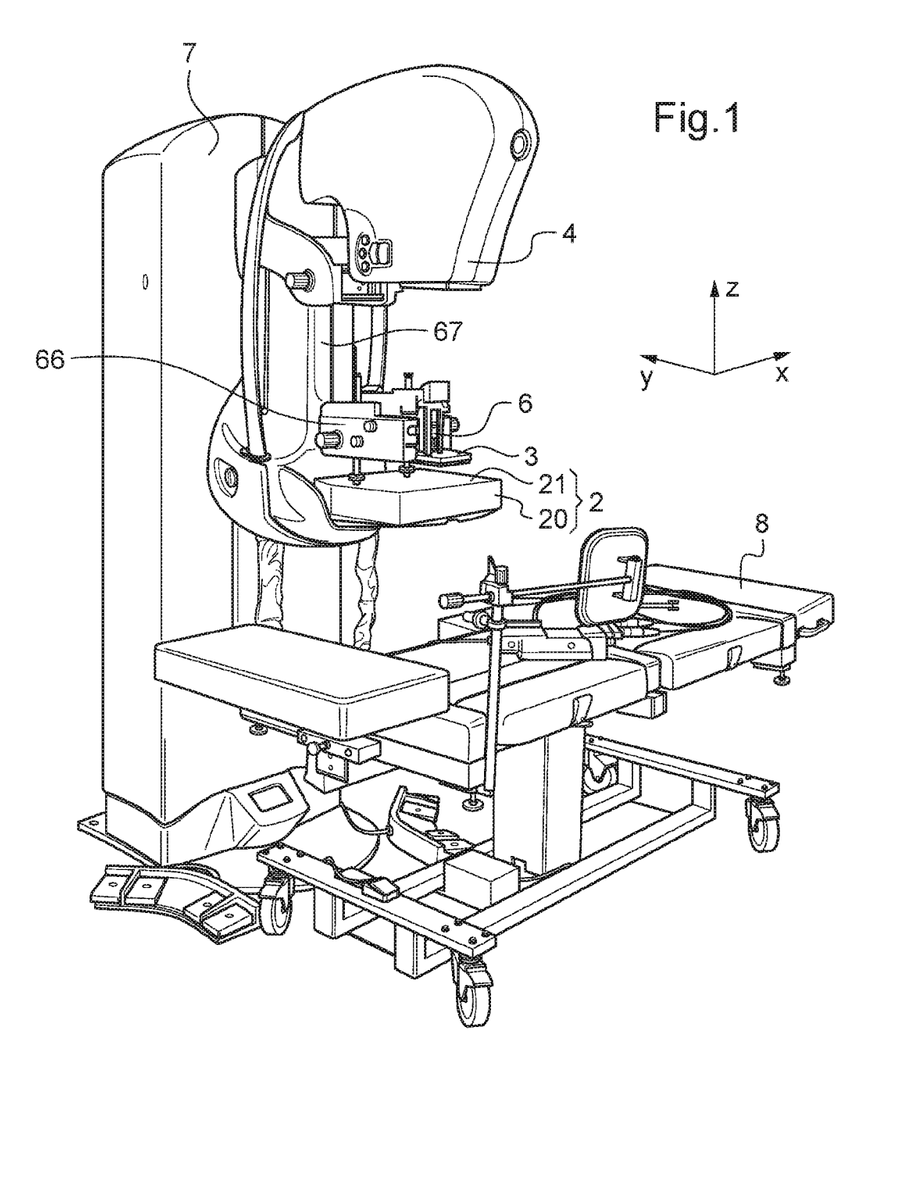
FIG. 1 shows a perspective view of an example of an apparatus including a biopsy device according to one embodiment of the invention and adapted to perform the biopsy method according to one embodiment of the invention.

FIG. 1 shows a perspective view of an example of an apparatus including a biopsy device according to one embodiment of the invention and adapted to perform the biopsy method according to one embodiment of the invention. There is a patient table 8, on which a patient may lie, which is movable so as to come close to an apparatus 7 including a biopsy system and an imaging system.

This apparatus 7 including a biopsy system and an imaging system comprises a radiation source 4, a detector 2 which here plays the part of the breast support. The biopsy holder 66 holds the biopsy sampler guide 6. The biopsy holder 66 is mounted on the imaging system 67. The biopsy sampler guide 6 is movable in all directions relative to the biopsy holder 66. Indeed, biopsy sampler guide 6 may perform translations in X, Y and Z directions relative to the biopsy holder 66. Besides or instead of said translations, there could be rotations.

The imaging system includes a detector 2 which presents a sensitive surface 21 parallel to the XY plane and a chest wall 20 parallel to the ZX plane.

The biopsy holder 66 is mounted on the imaging system 67. The biopsy holder 66 comprises a paddle 3. The breast of the patient lying on the patient table 8 will be compressed between the paddle 3 and the detector 2. The radiation source 4 is adapted to image part of the compressed breast including the lesion on the sensitive surface 21 of the detector 2, in order to localize the lesion in the breast. Once the lesion is localized, the biopsy sampler guide 6 will move to perform a biopsy in the localized lesion of the breast compressed between paddle 3 and detector 2. The biopsy will indeed be performed after the biopsy sampler guide has reached its final position and after the gun with its needle is introduced and secured in the biopsy sampler guide in its final position.

Figure 2A:
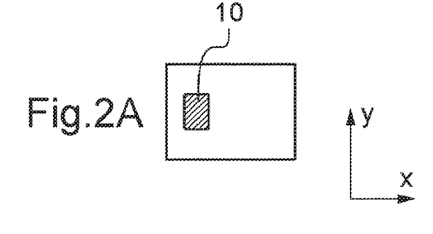
FIG. 2A shows a top view of an example of a biopsy window in a biopsy volume used in a biopsy method according to one embodiment of the invention.

FIG. 2A shows a top view of an example of a biopsy window in a biopsy volume used in a biopsy method according to one embodiment of the invention. The biopsy window 10 is the surface needed by the biopsy sampler guide to enter within the biopsy volume.

Figure 2B:
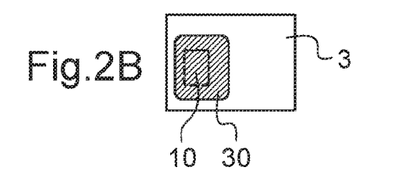
FIG. 2B shows a top view of an example of a paddle comprising a hole encompassing the biopsy window in a biopsy volume used in a biopsy method according to one embodiment of the invention.

FIG. 2B shows a top view of an example of a paddle comprising a hole encompassing the biopsy window in a biopsy volume used in a biopsy method according to one embodiment of the invention. A paddle 3 comprises a hole 30. The biopsy window 10 is encompassed in the hole 30. Therefore, the biopsy sampler guide can go through the hole 30 and then may move within the biopsy volume located between the paddle 3 and the detector 2.

Figure 2C:
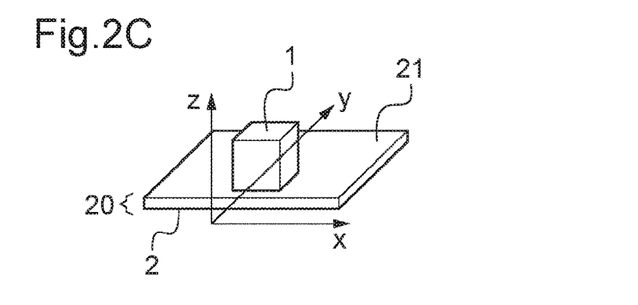
FIG. 2C shows a perspective view of an example of a biopsy volume used in a biopsy method according to one embodiment of the invention.

FIG. 2C shows a perspective view of an example of a biopsy volume used in a biopsy method according to one embodiment of the invention. The detector 2 presents a sensitive surface 21 in the plane XY, as well as a chest wall 20 in the plane ZX. The biopsy volume 1 is located on the surface 21 of the detector 2, close to the chest wall 20.

Figure 2D:
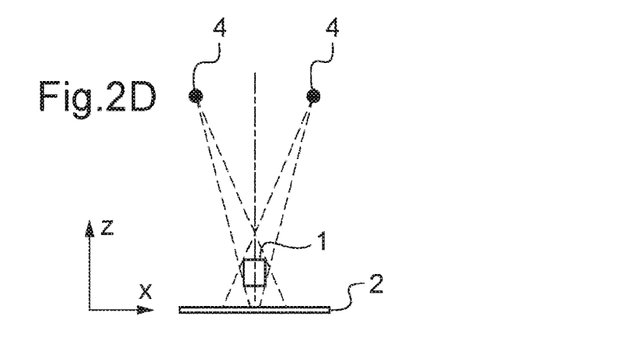
FIG. 2D shows a face view of an example of image acquisition of the biopsy volume related to the biopsy method according to one embodiment of the invention.

FIG. 2D shows a face view of an example of image acquisition of the biopsy volume related to the biopsy method according to one embodiment of the invention. There is one radiation source 4 which will have two different positions angularly shifted to each other, here plus or minus 15 degrees relative to verticality. For each position of the radiation source 4, the biopsy volume 1 is imaged on the detector 2. Starting from these two 2D images of the biopsy volume 1, 3D coordinates of the lesion within the biopsy volume 1 are computed so as to localize the lesion within the biopsy volume 1 and then guide the biopsy sampler guide within the biopsy volume 1 in order to perform the biopsy of the localized lesion.

Figure 3A:
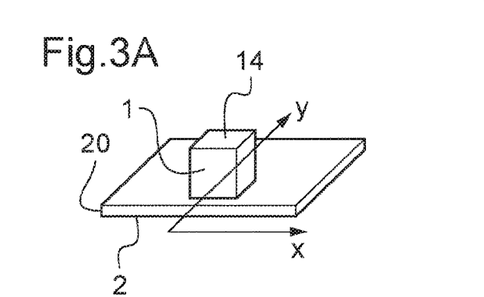
FIG. 3A shows a perspective view of a single and fixed position of a biopsy volume used in a biopsy method according to some prior art.

FIG. 3A shows a perspective view of a single and fixed position of a biopsy volume used in a biopsy method according to some prior art. There is only one fixed position 14 of the biopsy volume 1 on the detector 2, near the chest wall 20, centered in X direction.

Figure 3B:
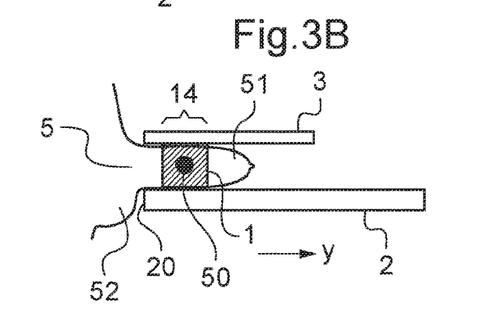
FIG. 3B shows a side view of an example of a large breast, with a lesion close to the nipple, positioned before performing a biopsy method according to some prior art.

FIG. 3B shows a side view of an example of a large breast, with a lesion close to the nipple, positioned before performing a biopsy method according to some prior art. The large breast 5 is compressed between the paddle 3 and the detector 2. There is a lesion 50, within the large breast 5, close to the nipple 51. The large breast 5 is positioned such that the lesion 50 is within the biopsy volume 1 which may be located only at one fixe position 14. Since the breast 5 is large and since the lesion 50 is located near the nipple 51, a big part 52 of the large breast 5 is not compressed between paddle 3 and detector 2, but remains hanging outside along the chest wall 20, what is very uncomfortable for the patient.

Figure 3C:
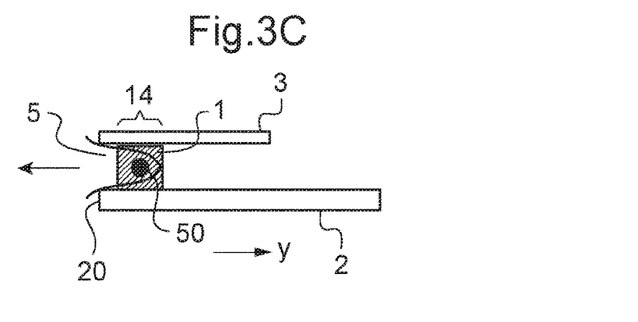
FIG. 3C shows a side view of an example of a small breast, with a lesion close to the nipple, positioned before performing a biopsy method according to some prior art.

FIG. 3C shows a side view of an example of a small breast, with a lesion close to the nipple, positioned before performing a biopsy method according to some prior art. The small breast 5 is compressed between the paddle 3 and the detector 2. There is a lesion 50, within the small breast 5, very close to the nipple 51. The small breast 5 is positioned such that the lesion 50 is within the biopsy volume 1 which may be located only at one fixe position 14. Since the breast 5 is small and since the lesion 50 is located very near the nipple 51, only a small part of the small breast 5 is compressed between paddle 3 and detector 2, what compels the small breast 5 to be pinched because not enough tissue can be compressed and what leads to the small breast 5 often squeezing out of the space between paddle 3 and detector 2, what is both unpractical for the radiologist in charge of the biopsy and painful for the patient.

Figure 3D:
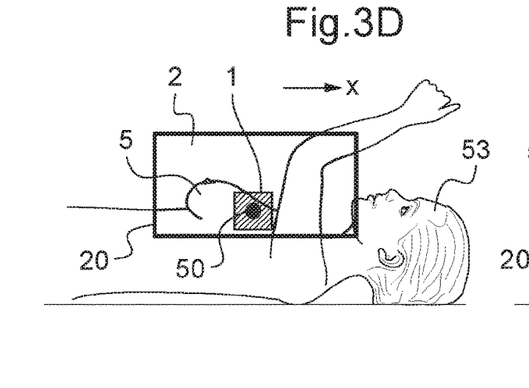
FIG. 3D shows a top view of an example of a breast, with a lesion in the upper part of the breast, positioned before performing a biopsy method according to some prior art.

FIG. 3D shows a top view of an example of a breast, with a lesion in the upper part of the breast, positioned before performing a biopsy method according to some prior art. The lesion 50 is on the top part of the breast 5. Since the biopsy volume 1 is fixed, centered in X direction and close to chest wall 20 in Y direction, the position of the patient has to adapt to this fixed biopsy volume 1. The position of the patient becomes then very uncomfortable because the upper part 53 of her body, for example her head and/or her shoulder, can be located over the detector 2.

Figure 3E:
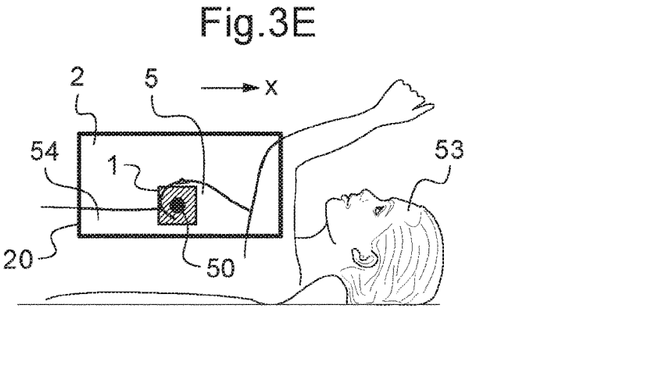
FIG. 3E shows a top view of an example of a breast, with a lesion in the lower part of the breast, positioned before performing a biopsy method according to some prior art.

FIG. 3E shows a top view of an example of a breast, with a lesion in the lower part of the breast, positioned before performing a biopsy method according to some prior art. The lesion 50 is on the bottom part of the breast 5. Since the biopsy volume 1 is fixed, centered in X direction and close to chest wall 20 in Y direction, the position of the patient has to adapt to this fixed biopsy volume 1. The position of the patient becomes then uncomfortable because the lower part 54 of her body, for example her belly and/or her hip, can be located over the detector 2.

Figures 4A, 4B, 4C:
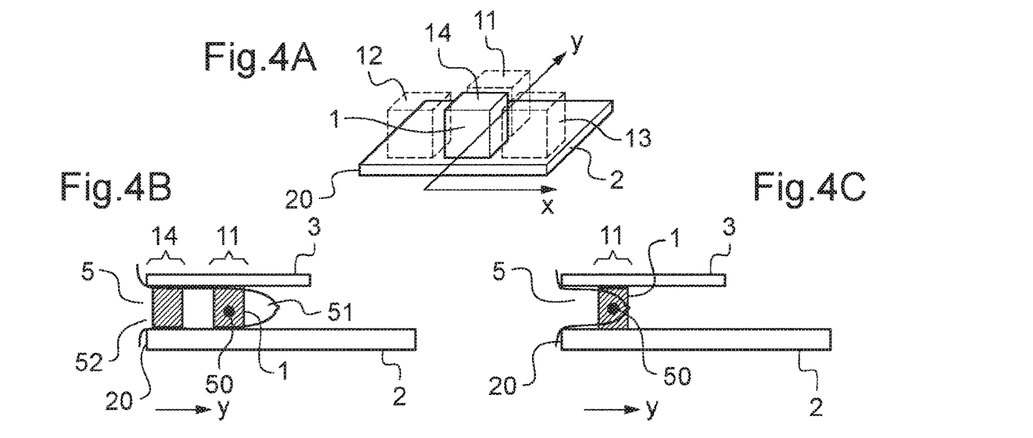
FIG. 4A shows a perspective view of variable positioning of a biopsy volume used in a biopsy method according to one embodiment of the invention.
FIG. 4B shows a side view of an example of a large breast, with a lesion close to the nipple, positioned before performing a biopsy method according to one embodiment of the invention.
FIG. 4C shows a side view of an example of a small breast, with a lesion close to the nipple, positioned before performing a biopsy method according to one embodiment of the invention.

FIG. 4A shows a perspective view of variable positioning of a biopsy volume used in a biopsy method according to one embodiment of the invention. There is not only one fixed position 14 of the biopsy volume 1 on the detector 2 as in the case of FIG. 3A, but on the contrary, there are several positions, here for example several discrete positions. There is the position 14 of the biopsy volume 1, located near the chest wall 20, centered in X direction. There are the positions 12 and 13 of the biopsy volume 1, located near the chest wall 20, respectively on the left and on the right of the centered position in X direction. There is the position 11 of the biopsy volume 1, located far from the chest wall 20, centered in X direction. There are also two other positions of the biopsy volume 1, not represented on FIG. 4A for clarity reasons, which are located far from the chest wall 20, at the same Y position than the position 11, respectively on the left and on the right of the centered position in X direction, at the same X positions than the positions 12 and 13. With a movable biopsy volume 1, the biopsy system adapts to the patient, which facilitates a lot the relative positioning of the patient breast 5 and of the biopsy volume 1. The patient position becomes more comfortable and the patient positioning also becomes easier for the radiologist, sparing time for everybody.

FIG. 4B shows a side view of an example of a large breast, with a lesion close to the nipple, positioned before performing a biopsy method according to one embodiment of the invention. The large breast 5 is compressed between the paddle 3 and the detector 2. There is a lesion 50, within the large breast 5, close to the nipple 51. The large breast 5 is positioned such that the lesion 50 is within the biopsy volume 1 at the position 11 this time and no more at the position 14 like on FIG. 3B. Now, thanks to the new position 11 of the biopsy volume, although the breast 5 is large and although the lesion 50 is located near the nipple 51, most of the large breast 5 is compressed between paddle 3 and detector 2 and no part of it remains hanging outside. This is all much more comfortable for the patient.

FIG. 4C shows a side view of an example of a small breast, with a lesion close to the nipple, positioned before performing a biopsy method according to one embodiment of the invention. The small breast 5 is compressed between the paddle 3 and the detector 2. There is a lesion 50, within the small breast 5, very close to the nipple 51. The small breast 5 is positioned such that the lesion 50 is within the biopsy volume 1 at the position 11 this time and no more at the position 14 like on FIG. 3C. Now, thanks to the new position 11 of the biopsy volume, although the breast 5 is small and although the lesion 50 is located very near the nipple 51, the whole small breast 5 is compressed between paddle 3 and detector 2 giving sufficient flesh to be compressed avoiding thereby squeezing out and pinching as in the biopsy system of FIG. 3C. This is both much more practical for the radiologist in charge of the biopsy and much more comfortable for the patient.

Figure 4D:
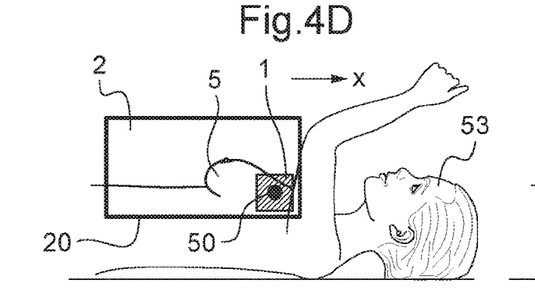
FIG. 4D shows a top view of an example of a breast, with a lesion in the upper part of the breast, positioned before performing a biopsy method according to one embodiment of the invention.

FIG. 4D shows a top view of an example of a breast, with a lesion in the upper part of the breast, positioned before performing a biopsy method according to one embodiment of the invention. The lesion 50 is on the top part of the breast 5. Since now the biopsy volume 1 can be moved from position 14 to position 13 to the right of X direction, the position of the patient no more needs to adapt to the position 14. The position of the patient is much more comfortable because the upper part 53 of her body, for example her head and/or her shoulder, is no more over the detector 2.

Figure 4E:
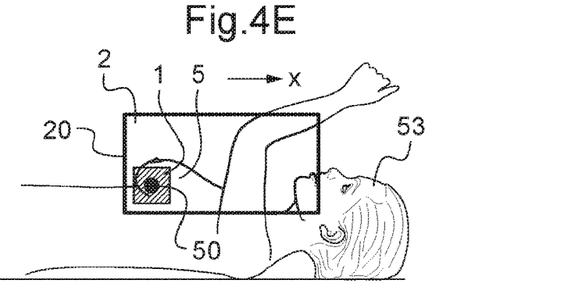
FIG. 4E shows a top view of an example of a breast, with a lesion in the lower part of the breast, positioned before performing a biopsy method according to one embodiment of the invention.

FIG. 4E shows a top view of an example of a breast, with a lesion in the lower part of the breast, positioned before performing a biopsy method according to one embodiment of the invention. The lesion 50 is on the bottom part of the breast 5. Since now the biopsy volume 1 can be moved from position 14 to position 12 to the left of X direction, the position of the patient no more needs to adapt to the position 14. The position of the patient is much more comfortable because the lower part 54 of her body, for example her belly and/or her hip, is no more over the detector 2.

Figure 5A:
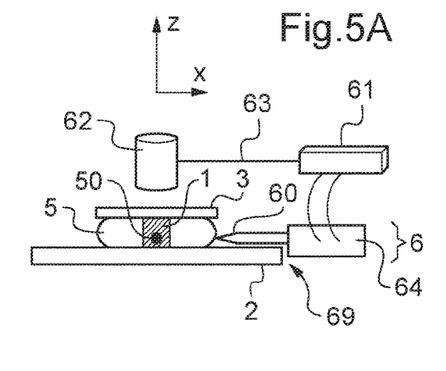
FIG. 5A shows a face view of a problem generated by a lateral approach of a biopsy sampler guide during a biopsy method according to some prior art.

FIG. 5A shows a face view of a problem generated by a lateral approach of a biopsy sampler guide during a biopsy method according to some prior art. A breast 5 including a lesion 50 is compressed between a paddle 3 and a detector 2, with a fixed biopsy volume 1 in a position centered in X direction. A biopsy sampler has a needle 60 supported by a gun 64 which are secured in the biopsy sampler guide 6. The biopsy sampler guide 6 is solidary attached with a slide 61 sliding in X direction on a rail 63 itself solidary attached with a holder 62. For thin breasts 5 or when the lesion 50 is near the detector 2, the radiologist cannot perform a biopsy in vertical approach because the tip of the needle 60 of the biopsy sampler would hit the detector 2. Therefore, the radiologist may prefer performing a lateral approach. When performing the lateral approach, slide 61 slides on rail 63 so that the biopsy sampler approaches laterally the breast 5 in order to reach the lesion 50. However, in this last case, the gun 64 often collides with the detector 2. Potential zone of collision is hereby referenced 69.

Figure 5B:
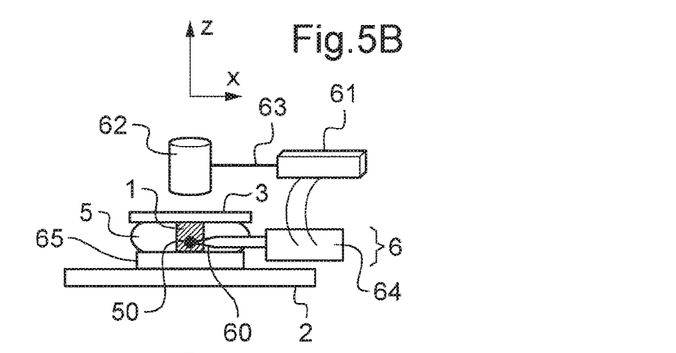
FIG. 5B shows a face view of a chock positioned below the breast in order to circumvent the problem generated by a lateral approach of a biopsy sampler guide during a biopsy method according to some prior art.

FIG. 5B shows a face view of a chock positioned below the breast in order to circumvent the problem generated by a lateral approach of a biopsy sampler during a biopsy method according to some prior art. A breast 5 including a lesion 50 is compressed between a paddle 3 and a detector 2, with a fixed biopsy volume 1 in a position centered in X direction. But here, the breast 5 is not directly compressed between paddle 3 and detector 2. Here, the radiologist uses a trick. Indeed, a chock 65 is placed under the breast 5, between breast 5 and detector 2. Therefore, the gun 64 no more collides with the detector 2, and on the contrary may reach the lesion 50 to allow the needle 60 to perform the biopsy in the lesion 50. However, this chock 50, often a kind of box, on the one side is rather uncomfortable for the patient and on the other side is a supplementary accessory requiring additional manipulation from the radiologist. Instead of using a chock 65 in the shape of a box, the radiologist may also use a membrane in which the breast 5 is rolled so as to increase the thickness of the breast 5 and the height of the lesion 50 with respect to the level of the detector 2.

Figure 5C:
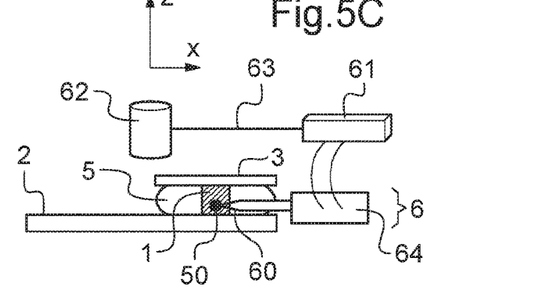
FIG. 5C shows a face view of an example of a solution solving the problem generated by a lateral approach of a biopsy sampler guide during a biopsy method according to one embodiment of the invention.

FIG. 5C shows a face view of an example of a solution solving the problem generated by a lateral approach of a biopsy sampler guide during a biopsy method according to one embodiment of the invention. A breast 5 including a lesion 50 is compressed between a paddle 3 and a detector 2, with a biopsy volume 1 displaced to an extreme position in X direction. Here, the breast 5 is directly compressed between paddle 3 and detector 2. No more need for a trick using a chock 65. Thanks to the extreme position of the displaced biopsy volume 1, the gun 64 no more collides with the detector 2, and on the contrary may easily reach the lesion 50 to allow the needle 60 to perform the biopsy in the lesion 50. The comfort is optimized for the patient and the manipulation is reduced for the radiologist.

This embodiment of the invention, shown on FIG. 5C, presents an advantage of allowing biopsy performance for any size of breast 5, without adding accessories to increase the thickness of the breast 5, only by moving the biopsy volume 1 at a side of the detector 2. If the breast 5 is a very thin breast, or if the lesion 50 is located quite near the detector 2, this mobility of the biopsy volume 1 can be used to place the biopsy volume 1 near a corner of the detector 2. In this last case, there will be no more collision between the gun 64 and the detector 2 and the biopsy can be performed without any additional manipulation of the breast 5 from the radiologist.

Figure 6:
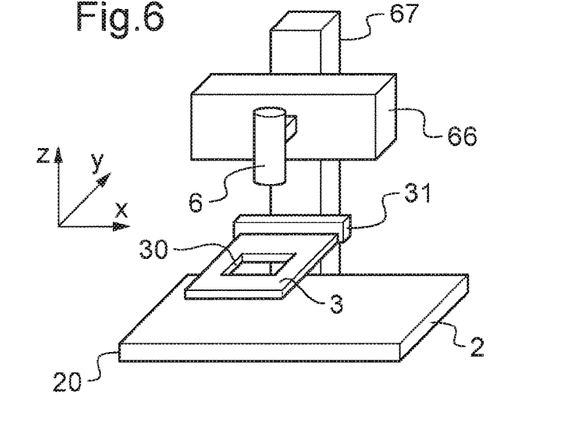
FIG. 6 shows a perspective view of an example of a biopsy mechanism used to perform the biopsy method according to a first embodiment of the invention.

FIG. 6 shows a perspective view of an example of a biopsy mechanism used to perform the biopsy method according to a first embodiment of the invention. The apparatus comprising the biopsy system includes an imaging system 67. A biopsy holder 66 is fixed relative to the detector 2 in the plane XY but is movable relative to detector 2 along the Z direction. The detector 2 is solidary attached with the imaging system 67. A biopsy sampler guide 6 is held by the biopsy holder 66. The biopsy sampler guide 6 may move relative to the biopsy holder 66, with translations of large extent, with respect to all directions X, Y and Z. It may also perform rotations. A paddle 3 is movingly, in the X,Y,Z directions in regards to detector 2, attached to a support 31. The support 31 is solidary attached with the imaging system 67, fixed in the plane XY of the detector 2 but is movable relative along the Z direction of the detector 2. The paddle 3 includes a hole 30. The space located between the hole 30 and the detector 2 constitutes the biopsy volume. The translational degrees of freedom of the paddle 3 in the plane XY relative to the detector 2 allows to displace the biopsy volume on the surface of the detector 2.

Figure 7A:
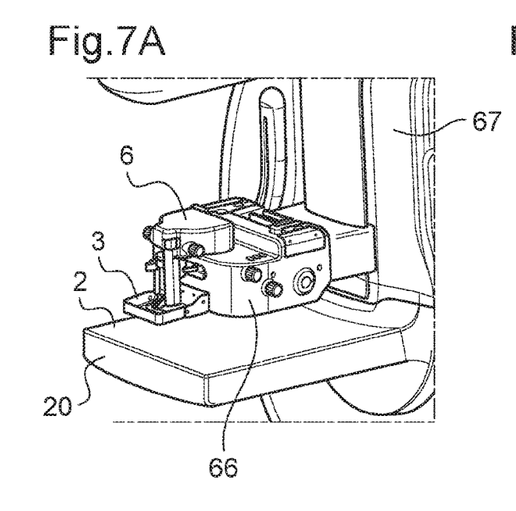
FIGS. 7A and 7B show perspective views of an example of a biopsy mechanism used to perform the biopsy method according to a second embodiment of the invention.
Figure 7B:
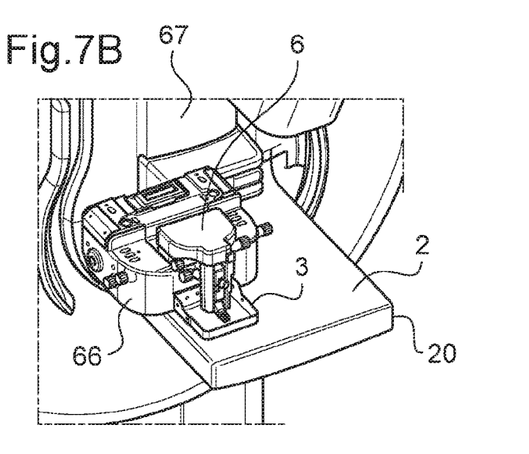

FIGS. 7A and 7B show perspective views of an example of a biopsy mechanism used to perform the biopsy method according to a second embodiment of the invention. The apparatus comprising the biopsy system includes an imaging system. A biopsy holder 66 is attached with the imaging system 67. The biopsy holder 66 is movable relative to the detector 2 with translations of large extent, with respect to all directions X, Y and Z. A biopsy sampler guide 6 is held by the biopsy holder 66. The biopsy sampler guide 6 may move relative to the biopsy holder 66, with translations of limited extent, with respect to all directions X, Y and Z. It may also perform rotations. A paddle 3 is solidary fixed to the biopsy holder 66. The paddle 3 includes a hole 30. The space located between the hole 30 and the detector 2 constitutes the biopsy volume. The translational degrees of freedom of the block comprising biopsy holder 66 and paddle 3 in the plane XY relative to the detector 2 allows to displace the biopsy volume on the surface of the detector 2.

Figure 8:
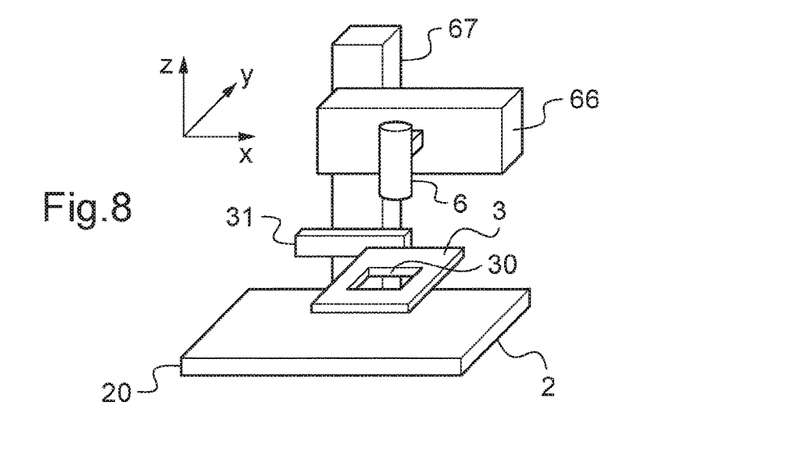
FIG. 8 shows a perspective view of an example of a biopsy mechanism used to perform the biopsy method according to a third embodiment of the invention.

FIG. 8 shows a perspective view of an example of a biopsy mechanism used to perform the biopsy method according to a third embodiment of the invention. The apparatus comprising the biopsy system includes an imaging system 67. A biopsy holder 66 is attached with the imaging system 67. The biopsy holder 66 is movable relative to the detector 2 with translations of large extent, with respect to all directions X, Y and Z. A biopsy sampler guide 6 is held by the biopsy holder 66. The biopsy sampler guide 6 may move relative to the biopsy holder 66, with translations of large extent, with respect to all directions X, Y and Z. It may also perform rotations. A paddle 3 is movingly, in the plane XY, attached to a support 31. The support 31 is solidary attached with the imaging system 67 fixed in the plane XY of the detector 2 but is movable relative to the detector 2 along the Z direction. The paddle 3 includes a hole 30. The space located between the hole 30 and the detector 2 constitutes the biopsy volume. The translational degrees of freedom of the paddle 3 in the plane XY relative to the detector 2 allows to displace the biopsy volume on the surface of the detector 2.

Figure 9A:
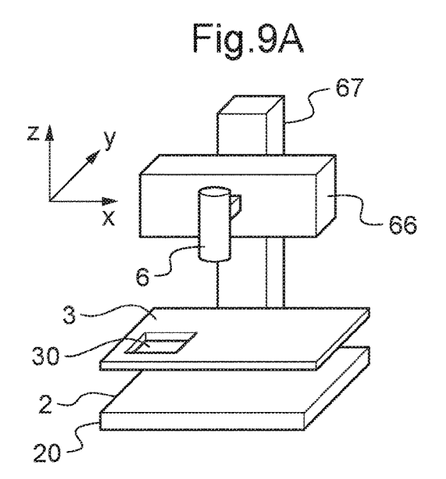
FIGS. 9A, 9B and 9C, show perspective views of an example of a biopsy mechanism used to perform the biopsy method according to a fourth embodiment of the invention.
Figure 9B:
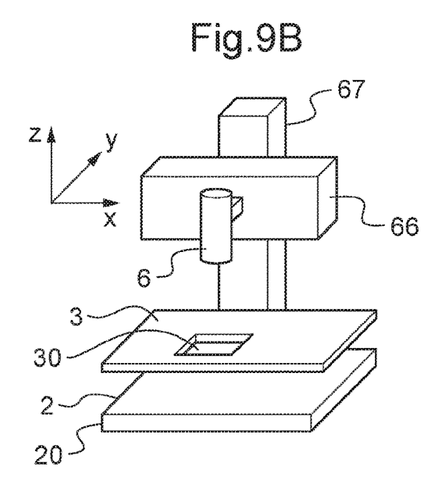
Figure 9C:
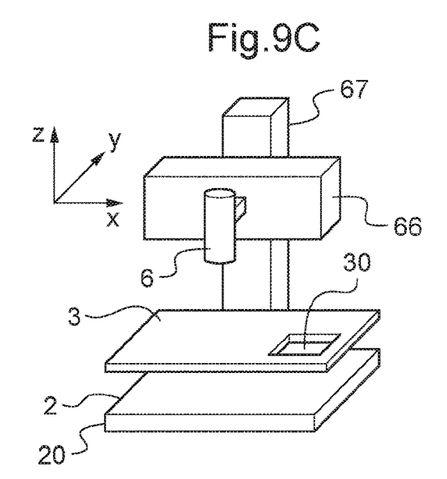

FIGS. 9A, 9B and 9C, show perspective views of an example of a biopsy mechanism used to perform the biopsy method according to a fourth embodiment of the invention. The apparatus comprising the biopsy system includes an imaging system 67. A biopsy holder 66 is mounted on the imaging system 67 A biopsy sampler guide 6 is held by the biopsy holder 66. The biopsy sampler guide 6 may move relative to the biopsy holder 66, with translations and rotations, with respect to all directions X, Y and Z. A paddle 3 will be chosen and attached with the imaging system 67 This paddle 3 can be chosen among a set of paddles 3 having their respective hole 30 disposed at a different place for each paddle 3. For example, the paddle 3 of FIG. 9A presents a hole 30 located near the chest wall 20 and at left side of detector 2. For example, the paddle 3 of FIG. 9B presents a hole 30 located near the chest wall 20 and at right side of detector 2. For example, the paddle 3 of FIG. 9C presents a hole 30 located near the chest wall 20 and centered in X direction. In a first option, the set of paddles may comprise for example three other paddles with X locations corresponding to the ones of FIGS. 9A, 9B and 9C, but with an Y location far from the chest wall 20. In a second alternative option, just by rotating half turn around Z direction the set of paddles represented on FIGS. 9A, 9B and 9C, one can get paddles with an Y location far from the chest wall 20, as explained in more detail with respect to FIGS. 11A and 11B. The space located between the hole 30 and the detector 2 constitutes the biopsy volume. The different locations of the hole 30 in the different paddles 3 of the set of paddles allows to displace the biopsy volume on the surface of the detector 2, simply by changing the paddle 3.

Figure 10:
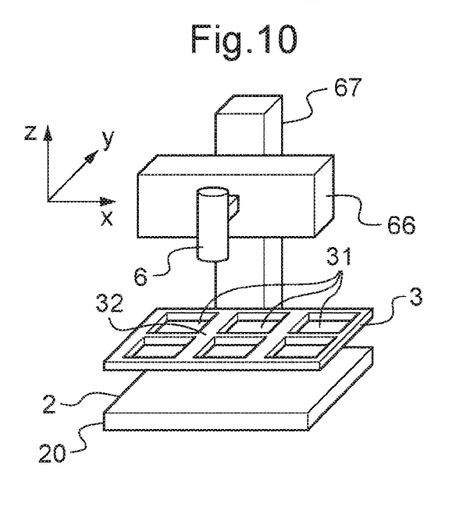
FIG. 10 shows a perspective view of an example of a biopsy mechanism used to perform the biopsy method according to a fifth embodiment of the invention.

FIG. 10 shows a perspective view of an example of a biopsy mechanism used to perform the biopsy method according to a fifth embodiment of the invention. The apparatus comprising the biopsy system includes an imaging system 67. A biopsy holder 66 is mounted on the imaging system 67. A biopsy sampler guide 6 is held by the biopsy holder 66. The biopsy sampler guide 6 may move relative to the biopsy holder 66, with translations and rotations, with respect to all directions X, Y and Z. A paddle 3 includes six holes 31, respectively disposed near the chest wall 20, at left, centered and right side of detector 2, and far from the chest wall 20, at left, centered and right side of detector 2. Located between the holes 31, the crossings 32 push on the breast under examination in a rather uncomfortable or even painful way for the patient. Each of the spaces located between the holes 31 and the detector 2 may constitute the biopsy volume. The different holes 31 allow displacing the biopsy volume on the surface of the detector 2, simply by changing the chosen hole 31 on the paddle 3.

Figure 11A:
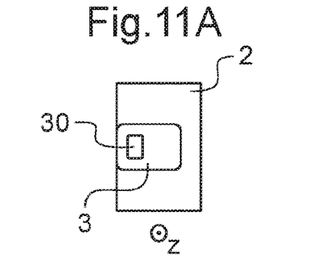
FIGS. 11A and 11B show top views of an example of a biopsy mechanism used to perform the biopsy method according to a sixth embodiment of the invention.
Figure 11B:
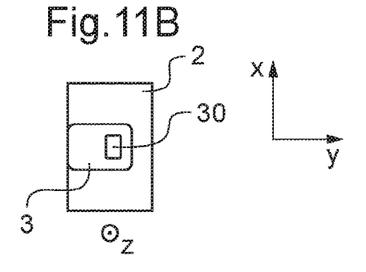

FIGS. 11A and 11B show top views of an example of a biopsy mechanism used to perform the biopsy method according to a sixth embodiment of the invention. The paddle 3 of FIG. 11A presents a biopsy volume under the hole 30 which is X centered and located near the chest wall 20 with respect to direction Y. Simply by rotating half turn this paddle 3 around Z direction, one gets the paddle 3 of FIG. 11B which biopsy volume under the hole 30 is X centered and which is located far from the chest wall 20 with respect to Y direction. This paddle rotation can be kept manual as explained just above or can even be made automat FIGS. 12A and 12B show perspective views of respectively discrete and continuous ways of variable positioning of a biopsy volume used to perform the biopsy method according to one embodiment of the invention.

Figure 12A:
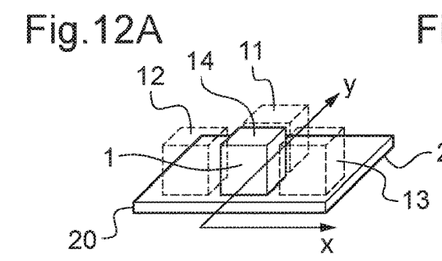
FIGS. 12A and 12B show perspective views of respectively discrete and continuous ways of variable positioning of a biopsy volume used to perform the biopsy method according to one embodiment of the invention.

On FIG. 12A, several discrete positions 11 to 14 of the biopsy volume 1 are to be seen, as already explained with respect to FIG. 4A. This discrete variation of biopsy volume 1 positioning is simpler to synchronize with the radiation source position variations than the continuous variation of FIG. 12B.

Figure 12B:
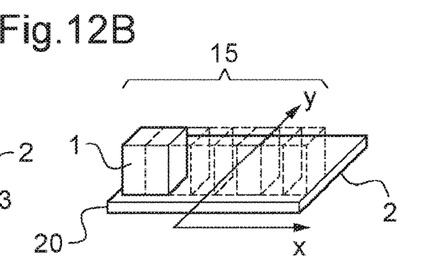

On FIG. 12B, along X direction, the biopsy volume 1 may move continuously along X direction, here near the chest wall 20 but same continuous variation along X direction far from the chest wall 20 may be provided in addition too. This biopsy volume 1 presents a continuously varying position 15 along X direction which is more fully optimized than the discrete variation of FIG. 12A, with respect to relative position of breast and detector 2, thereby ensuring minimal manipulation for the radiologist and maximal comfort for the patient.

With both systems of FIGS. 12A and 12*b*, if the lesion of the breast is not in the biopsy volume 1 at the first trial, the radiologist can use the biopsy volume 1 positioning variability to reposition the lesion in the biopsy volume 1, while the breast remains at the same position, instead of manipulating the breast to position the lesion into a fixed biopsy volume 1 as in prior art.

Figure 13A:
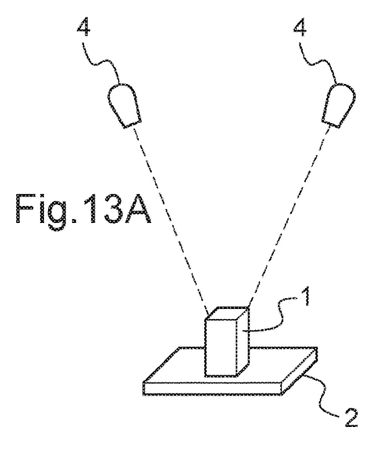
FIGS. 13A and 13B show perspective views of an example of image acquisition, with preset acquisition sequences, of the biopsy volume related to the biopsy method according to one embodiment of the invention.
Figure 13B:
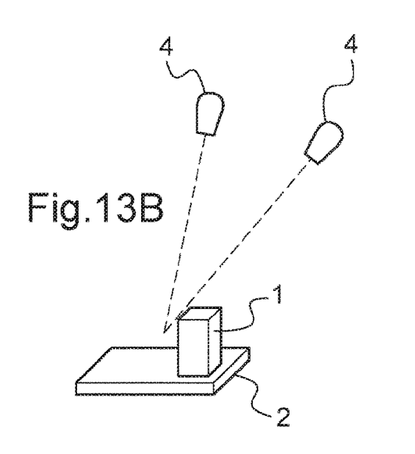

FIGS. 13A and 13B show perspective views of an example of image acquisition, with preset acquisition sequences, of the biopsy volume related to the biopsy method according to one embodiment of the invention.

On FIG. 13A, there is one radiation source 4 which will have two different positions angularly shifted to each other, here plus or minus 15 degrees relative to vertical for a biopsy volume 1 which is X centered. For each position of the radiation source 4, the biopsy volume 1 is imaged on the detector 2. Starting from these two 2D images of the biopsy volume 1, 3D coordinates of the lesion within the biopsy volume 1 are computed so as to localize the lesion within the biopsy volume 1 and then guide the biopsy sampler guide within the biopsy volume 1 in order to perform the biopsy of the localized lesion.

On FIG. 13B, for a biopsy volume 1 which is at one side of detector 2, here at right side, along X direction, both angular positions of the radiation source 4 are angularly shifted to the right. The extension of angular displacement of radiation source 4 should then be augmented. Image processing will be somewhat more complicated for right position of biopsy volume 1 on FIG. 13B than for the centered position of biopsy volume 1 on FIG. 13A, because of the lack of symmetry of the positions of the radiation source 4 with respect to verticality. In another option, the source 4 may be made movable by translation along X direction too, in addition to its angular displacement of then only limited extension, for example by being mounted on a rail parallel to X direction, so that the symmetry with respect to verticality may be kept, keeping thereby a rather simple image processing for the localization of the lesion within the breast.

Figure 13C:
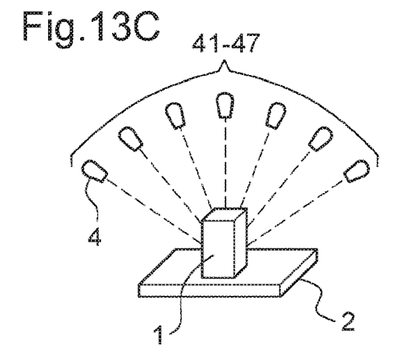
FIGS. 13C and 13D show perspective views of an example of image acquisition, with dynamically computed acquisition sequences, of the biopsy volume related to the biopsy method according to one embodiment of the invention.
Figure 13D:
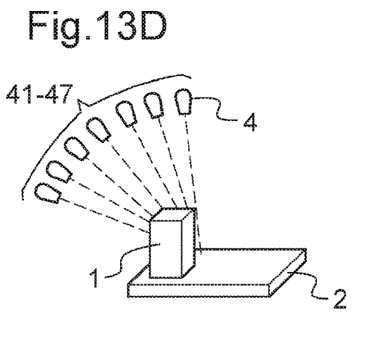

FIGS. 13C and 13D show perspective views of an example of image acquisition, with dynamically computed acquisition sequences, of the biopsy volume related to the biopsy method according to one embodiment of the invention.

On FIG. 13C, there is one radiation source 4 which will have several different positions 41 to 47 angularly shifted to one another, for a biopsy volume 1 which is X centered. For each position 41 to 47 of the radiation source 4, the biopsy volume 1 is imaged on the detector 2. Starting from these several 2D images of the biopsy volume 1, 3D coordinates of the lesion within the biopsy volume 1, as well as possibly complete 3D images, are computed so as to localize the lesion within the biopsy volume 1 and then guide the biopsy sampler guide within the biopsy volume 1 in order to perform the biopsy of the localized lesion.

On FIG. 13D, for a biopsy volume 1 which is at one side of detector 2, here at left side, along X direction, all angular positions 41 to 47 of the radiation source 4 are angularly shifted to the left. In one option, the sequences can be computed dynamically depending on the biopsy volume position. In another option, a preset of sequences can be previously computed and used depending on system configuration.

The invention has been described with reference to embodiments. However, many variations are possible within the scope of the invention.

The invention claimed is:

1. A biopsy method comprising:
    automated moving of at least part of a biopsy sampler within a biopsy volume to perform a biopsy in a zone of interest in a body,
    wherein said automated moving is preceded by variable positioning of said biopsy volume both along a first axis and a second axis both along a plane of a breast support, wherein the plane is parallel to a horizontal surface of the breast support, wherein the horizontal surface directly contacts and supports a portion of the body that includes the zone of interest, and wherein the first axis and the second axis are orthogonal to each other, and the variable positioning along both the first axis and the second axis occurs separately from each other.

2. The biopsy method according to claim 1, wherein said automated moving of at least part of said biopsy sampler within said biopsy volume is automated moving of a biopsy sampler guide.

3. The biopsy method according to claim 2, wherein said biopsy volume is included in a volume delimited by a hole in a paddle facing said breast support.

4. The biopsy method according to claim 3, wherein said paddle is moving relative to said breast support at least in the plane of said breast support and said paddle comprises at least one hole.

5. The biopsy method according to claim 4, wherein said biopsy sampler guide is linked by a biopsy holder to an imaging system comprising a detector, said biopsy holder is fixed relative to said breast support.

6. The biopsy method according to claim 4, wherein said biopsy sampler guide being linked by a biopsy holder to an imaging system comprising a detector, said biopsy holder is fixed relative to said paddle.

7. The biopsy method according to claim 4, wherein said biopsy sampler guide being linked by a biopsy holder to an imaging system comprising a detector, said biopsy holder is moving relative to said breast support and is moving independently from said paddle.

8. The biopsy according to claim 3, wherein said paddle is fixed relative to said breast support in the plane of said breast support.

9. The biopsy method according to claim 8, wherein said paddle comprises several holes at different places in the plane of said breast support, said variable positioning being obtained by choosing one hole of said several holes for said automated moving of said biopsy sampler guide.

10. The biopsy method according to claim 8, wherein said paddle comprises a single hole and the single hole is located at a given place in the plane of said breast support, there being a set of several paddles each having a respective single hole located at respective given places which are different from one another and being able to be alternatively set up, said variable positioning being obtained by choosing one paddle from said set of several paddles to utilize.

11. A biopsy device configured to perform the method of claim 1.

* * * * *